US006153649A

United States Patent [19]
Maignan

[11] Patent Number: 6,153,649
[45] Date of Patent: Nov. 28, 2000

[54] USE OF CARBOXYLIC ACIDS HAVING A SULPHUR FUNCTION FOR PROMOTING SKIN EXFOLIATION OR STIMULATING EPIDERMAL REGENERATION

[75] Inventor: Jean Maignan, Tremblay-en-France, France

[73] Assignee: L'Oreal, Paris, France

[21] Appl. No.: 09/065,100

[22] PCT Filed: Oct. 23, 1996

[86] PCT No.: PCT/FR96/01658

§ 371 Date: Apr. 29, 1998

§ 102(e) Date: Apr. 29, 1998

[87] PCT Pub. No.: WO97/16165

PCT Pub. Date: May 9, 1997

[30] Foreign Application Priority Data

Oct. 30, 1995 [FR] France .................................. 95 12787

[51] Int. Cl.[7] .................................................. A61K 31/85

[52] U.S. Cl. ......................... 514/557; 514/574; 514/846; 514/937; 424/401

[58] Field of Search .................................. 514/557, 574, 514/846, 937; 424/401

[56] References Cited

U.S. PATENT DOCUMENTS

| | | | |
|---|---|---|---|
| 4,363,815 | 12/1982 | Yu et al. | 424/274 |
| 4,539,320 | 9/1985 | Lang et al. | 514/222 |
| 4,696,946 | 9/1987 | Green et al. | 514/574 |
| 5,451,405 | 9/1995 | Zhang et al. | 424/401 |
| 5,866,168 | 2/1999 | Delacharriere et al. | 424/639 |

FOREIGN PATENT DOCUMENTS

WO 91/02538 3/1991 WIPO .

*Primary Examiner*—Jose' G. Dees
*Assistant Examiner*—Michael A. Williamson
*Attorney, Agent, or Firm*—Oblon, Spivak, McClelland, Maier & Neustadt, P.C.

[57] ABSTRACT

The use of carboxylic acids having a thioether function, a sulphoxide function or a sulphone function in or for making a cosmetic or dematological composition for promoting skin exfoliation and/or stimulating epidermal regeneration, is disclosed. The use of said composition for controlling intrinsic and extrinsic skin ageing, and a non-therapeutic skin treatment method useful for skin exfoliation, are also disclosed.

37 Claims, No Drawings

USE OF CARBOXYLIC ACIDS HAVING A SULPHUR FUNCTION FOR PROMOTING SKIN EXFOLIATION OR STIMULATING EPIDERMAL REGENERATION

This application is a 371 of PCT/FR96/01658 filed Oct. 23, 1996.

The invention relates to the use of carboxylic acids carrying a thioether function, a sulphoxide function or a sulphone function, in or for the production of a cosmetic and/or dermatological composition for promoting skin desquamation and/or combating intrinsic and extrinsic skin ageing. It also relates to a non-therapeutic skin treatment process for desquamating the skin as well as to a treatment process for cutaneous ageing.

Cutaneous ageing resulting from effects of intrinsic or extrinsic factors on the skin is shown by the appearance of wrinkles and lines, and the yellowing of the skin which develops a blotchy look accompanied by the appearance of pigmentary spots, by the disorganization of the elastin and collagen fibres causing a loss of elasticity, of suppleness and of firmness and by the appearance of telangiectases.

Some of these signs of ageing are more particularly connected with intrinsic or physiological ageing, that is to say to "normal" ageing connected with age, although others are more specific for extrinsic ageing, that is to say ageing generally caused by the environment; more particularly photo-ageing due to exposure to the sun, to light or to any other radiation.

The invention is concerned with intrinsic or physiological ageing as well as with extrinsic ageing.

The changes in the skin due to intrinsic ageing are the consequence of a genetically programmed senescence in which endogenous factors intervene. This intrinsic ageing causes, especially, a slowing down of the renewal of the cells of the skin, which is essentially reflected by the appearance of clinical changes such as the reduction in the subcutaneous adipose tissue and the appearance of fine wrinkles or lines, and by histopathological changes such as an increase in the number and the thickness of the elastic fibres, a loss of vertical fibres in the membrane of the elastic tissue, and the presence of large irregular fibroblasts in the cells of this elastic tissue.

In contrast, extrinsic ageing results in clinical alterations such as thick wrinkles and the formation of a flabby and tanned skin, and in histopathological changes such as excessive accumulation of elastic matter in the upper dermis and degeneration of the collagen fibres.

Various agents intended for combating cutaneous ageing are known in the prior art.

Thus, the patent U.S. Pat. No. 4,603,146 describes the use of retinoic acid and of its derivatives in cosmetic compositions, for the purpose of combating cutaneous ageing. However, many patents and publications (see, for example, the application EP-A-0413528) as well as numerous commercial cosmetic compositions teach the use of α-hydroxy acids such as lactic acid, glycolic acid or alternatively citric acid for treating cutaneous ageing.

Finally, β-hydroxy acids and more especially salicylic acid as well as its derivatives are known for their desquamating properties (see the documents WO-A-93/10756 and U.S. Pat. No. 4,767,750).

All these compounds have an action against ageing of the skin, consisting in desquamation, that is to say the elimination of "dead" cells situated at the surface of the *stratum corneum*. This desquamating property is also called, often wrongly, a keratolytic property. However, these compounds also have secondary effects, which consist of stinging, pulling, heating and redness, which are unpleasant for the user.

It is thus seen that the need exists for anti-ageing agents having an action which is at least as effective as that of the compounds of the prior art, but does not have their disadvantages.

The Applicant has unexpectedly found that the topical application of certain carboxylic acids carrying a thioether function, a sulphoxide function or a sulphone function, makes it possible to desquamate the skin as well as to stimulate epidermal cell renewal and epidermal repair.

Of course, carboxylic acids carrying a thioether function, a sulphoxide function or a sulphone function are already known in the cosmetic field in topical compositions for improving the elasticity of the skin (see the document EP-A-0576287). However, nobody to date has envisaged or suggested using these acids for the desquamation of the skin, the stimulation of epidermal renewal and the treatment of cutaneous ageing.

Consequently, a subject of the present invention is the use of carboxylic acids carrying a thioether function, a sulphoxide function or a sulphone function in the free state or at least partially neutralized, in or for the production of a cosmetic or dermatological composition for promoting desquamation of the skin and/or stimulating epidermal renewal.

A subject of the present invention is likewise the use of carboxylic acids carrying a thioether function, a sulphoxide function or a sulphone function in the free state or at least partially neutralized, in or for the production of a cosmetic or dermatological composition as anti-ageing agent, especially for combating wrinkles and/or lines and/or actinic spots and/or cutaneous dyschromias and/or dermitis and/or cicatrices.

A subject of the invention is more particularly the use of at least one carboxylic acid carrying a thioether function, a sulphoxide function or a sulphone function, in the free state or at least partially neutralized, in or for the production of a cosmetic or dermatological composition for promoting desquamation of the skin and/or stimulating epidermal renewal, this acid corresponding to one of the following formulae (I), (II) or (III):

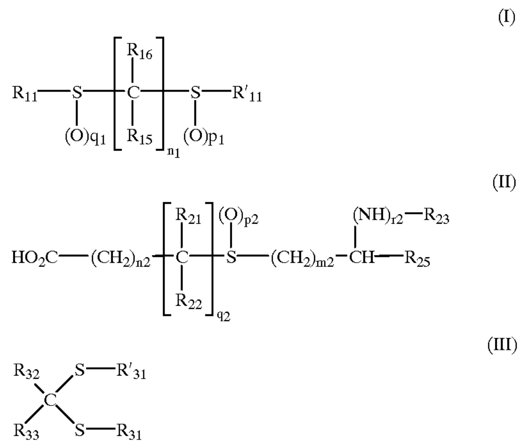

in which $n_1$ is an integer of a value ranging from 1 to 10, $p_1$ and $q_1$, which are identical or different, are 0, 1 or 2, $n_2$ is an integer of a value ranging from 0 to 5, $p_2$ is 0, 1 or 2, $q_2$ is 0, 1, 2 or 3, $m_2$ is an integer of a value ranging from 0 to 10, $r_2$ is 0 or 1, $q_2$ and $n_2$ never both being zero simultaneously, $R_{11}$ and $R'_{11}$, which are identical or different, are a radical chosen from the group formed by:

a)

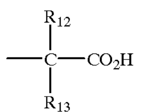

b)

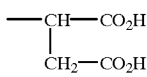

c)

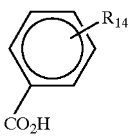

in which $R_{12}$ and $R_{13}$, which are identical or different, are chosen from the group formed by the hydrogen atom and $C_1$–$C_8$ linear or branched alkyl or alkenyl radicals; $R_{14}$ is chosen from the group formed by the hydrogen atom, linear or branched $C_1$–$C_8$ alkyl radicals, linear or branched $C_1$–$C_8$ alkenyl radicals and linear or branched $C_1$–$C_8$ alkoxy radicals; $R_{15}$ and $R_{16}$ are chosen from the group formed by the hydrogen atom and linear or branched $C_1$–$C_8$ alkoxy radicals; $R_{21}$ and $R_{22}$ are chosen from the group formed by the hydrogen atom and linear or branched $C_1$–$C_6$ alkoxy and alkenyl radicals, phenyl, $C_1$–$C_6$ alkylcarboxylic and $C_1$–$C_6$ alkenylcarboxylic acid radicals; $R_{23}$ is a $C_1$–$C_{17}$ linear or branched alkyl or alkenyl radical or an acyl radical —CO—$R_{24}$, where $R_{24}$ is a $C_1$–$C_{17}$ linear or branched alkyl or alkenyl radical; $R_{25}$ is chosen from the hydrogen atom, the $C_1$–$C_6$ linear or branched alkyl and alkenyl radicals, a $C_1$–$C_5$ alkyl-carboxylic acid radical, $C_1$–$C_5$ alkenylcarboxylic acid radical and the function —COOH; $R_{31}$ and $R'_{31}$ are chosen from the group formed from the radicals:

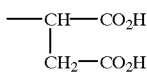

and

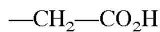

$R_{32}$ is a radical chosen from the group formed from:

i) —$CH_3$ ii) —$CO_2H$ iii)

iv)

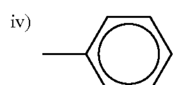

v)

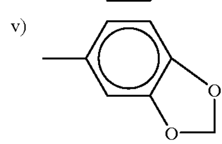

-continued vi)

vii)

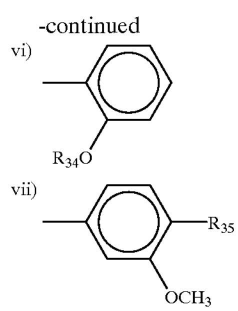

such that $R_{34}$ is a radical chosen from: —$CH_2$—$CO_2H$ and —CO—$CH_3$ and $R_{35}$ is a radical chosen from : OH, $OCH_3$, $OC(CH_3)_3$, $OCH_2CO_2H$ $R_{33}$ is a radical chosen from the group formed from: the hydrogen atom, a $C_1$–$C_8$ linear or branched alkyl or alkenyl radical, or $R_{32}$ and $R_{33}$ together form an alkane-diyl radical —$(CH_2)m_3$—such that $m_3$ represents an integer of a value ranging from 3 to 5, or $R_{32}$ and $R_{33}$ together form an aralkanediyl radical

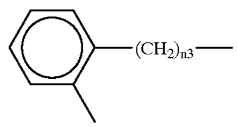

such that $n_3$ is 3 or 4.

The compounds which can be used according to the invention likewise comprise the mono- and the disalts of the products described above, it being possible to choose these salts from the alkali metal salts, alkaline earth metal salts and the organic amine salts. By way of example, sodium salts, potassium, magnesium, calcium and strontium salts, ethanolamine, diethanolamine and triethanolamine salts, and lysine and arginine salts will be mentioned.

The desquamation of the skin is associated with a clinical improvement in the quality of the skin which becomes more radiant, less wrinkled and generally younger. In addition, the use of the acids described above allows imperfections in the skin such as spots, cutaneous dyschromias, dermitis, actinic lentigos, cicatrices and cicatricial pigmentations to be treated.

Consequently, a subject of the invention is also the use of at least one carboxylic acid carrying a thioether function, a sulphoxide function or a sulphone function and especially an acid corresponding to one of the formulae (I), (II) or (III) in the free state or at least partially neutralized, in or for the production of a cosmetic or dermatological composition as anti-ageing agent, especially for combating wrinkles and/or lines and/or actinic spots and/or cutaneous dyschromias and/or dermitis and/or cicatrices.

The Applicant has particularly noted, without this being completely explained, that the compounds have anti-ageing action which is at least as effective as the compounds of the prior art and that this action is milder in so far as no irritation is experienced and no redness is observed when a cosmetic or dermatological composition containing them is applied to the skin.

Preferentially, the acids of the invention will be chosen from:

a) the compounds corresponding to the formula (I) in which $R_{15}=R_{16}=H$, $p_1=q_1$ and $R_{11}=R'_{11}$, b) the compounds corresponding to the formula (II) in which:

$r_2$=1, $R_{23}$=H, $R_{25}$=—COOH and m=1 (cysteine derivatives) or m=2 (homocysteine derivatives)

c) the compounds corresponding to the formula (III) in which:

$R_{32}$ is an aromatic radical, $R_{33}$=H and R31=$R'_{31}$.

In particular, the acids of the invention are chosen from:

2,2'-dithiomethylenedibenzoic acid,
2,2'-dithioethylenedibenzoic acid,
2,2'-disulphinylethylenedibenzoic acid,
2,2'-(dithiopropane-1,3-diyl)dibenzoic acid,
2,2'-(dithiobutane-1,4-diyl)dibenzoic acid,
2,2'-(dithiopentane-1,5-diyl)dibenzoic acid,
2,2'-(dithiohexane-1,6-diyl)dibenzoic acid,
2,2'-(disulphinylhexane-1,6-diyl)dibenzoic acid,
α,α'-(dithiohexane-1,6-diyl)disuccinic acid,
2,2'-(dithiooctane-1,8-diyl)dibenzoic acid,
2,2'-(dithiodecane-1,10-diyl)dibenzoic acid,
α,α'-(dithiodecane-1,10-diyl)disuccinic acid,
α,α'-dithiomethylenediacetic acid,
α,α'-dithioethylenediacetic acid,
α,α'-disulphinylethylenediacetic acid,
α,α'-disulphonylethylenediacetic acid,
α,α'-(dithiohexane-1,6-diyl)diacetic acid,
α,α'-(disulphinylhexane-1,6-diyl)diacetic acid,
α,α'-(disulphonylhexane-1,6-diyl)diacetic acid,
α,α'-(dithiodecane-1,10-diyl)diacetic acid,
α,α'-(disulphinyldecane-1,10-diyl)diacetic acid,
α,α'-(disulphonyldecane-1,10-diyl)diacetic acid,
S-(carboxymethyl)cysteine,
S-(carboxyethyl)cysteine,
S-(4-carboxybutyl)cysteine,
S-(carboxymethyl)sulphinylcysteine,
S-(carboxymethyl)sulphonylcysteine,
S-(1-carboxy-1-ethyl)cysteine,
S-(2-carboxy-2-propyl)cysteine,
α,α'-(p-methoxybenzylidenedithio)disuccinic acid,
α,α'-(benzylidenedithio)disuccinic acid,
α,α'-(piperonylidenedithio)disuccinic acid,
α,α'-(vanillylidenedithio)disuccinic acid,
α,α'-(veratrylidenedithio)disuccinic acid,
α,α'-(4-butoxy-3-methoxybenzylidenedithio)disuccinic acid,
α,α'-(4-carboxymethyloxy-3-methoxybenzylidenedithio)-disuccinic acid,
α,α'-(p-methoxybenzylidenedithio)diacetic acid,
α,α'-(benzylidenedithio)diacetic acid,
α,α'-(piperonylidenedithio)diacetic acid,
α,α'-(vanillylidenedithio)diacetic acid,
α,α'-(veratrylidenedithio)diacetic acid, as well as their inorganic or organic base monosalts and disalts.

Preferably, according to the invention, S-carboxymethylcysteine as well as its inorganic or organic base mono- and disalts will be used.

The preparation of the products used according to the invention is well known to the person skilled in the art:

For the synthesis of the products corresponding to the formula (I), it is possible to refer to the document FR-2447189 in which this synthesis is described with $R_{15}$=$R_{16}$=H. The same synthesis methods are used in the cases where $R_{15}$ and $R_{16}$ are other radicals.

The synthesis of the products corresponding to the formula (II) with $p_2$=0 is described in the documents FR-1505874 and FR-1472021. When $p_2$=1, 2, the products corresponding to the formula (II) are prepared starting from corresponding thioethers by an oxidizing treatment according to the methods known to the person skilled in the art. It is possible, for example, to refer to the methods of oxidation of thioethers to sulphoxides and to sulphones described by Jerry March in "Advanced Organic Chemistry", Wiley Interscience, 3rd Edition p. 1089.

The synthesis of the products corresponding to the formula (III) has been described in the document FR-2468362.

In the compositions according to the invention, the acid or the mixture of carboxylic acids carrying a thioether function, a sulphoxide function or a sulphone function, and especially the products according to the formulae (I), (II) and (III), can be used in a quantity ranging from 0.2 to 20% by weight with respect to the total weight of the composition and in particular in a quantity ranging from 0.5 to 10% and, better, from 0.5 to 5% by weight with respect to the total weight of the composition.

The acids of the invention can be combined with other active agents known for their desquamating properties, such as hydroxy acids, α- or β-keto acids, and retinoids. Such a combination allows the active concentration of the latter to be decreased on account of additive effects. It is thus possible to obtain a less irritant and less toxic composition as well as a composition which is more effective than those of the prior art using only these active compounds.

The hydroxy acids can be, for example, α-hydroxy acids or β-hydroxy acids, which can be linear, branched or cyclic, saturated or unsaturated. The hydrogen atoms of the carbon chain, in addition, can be substituted by halogens, or halogenated, alkylated, acylated, acyloxylated, alkoxycarbonylated or alkoxylated radicals having from 2 to 18 carbon atoms.

These hydroxy acids are especially glycolic, lactic, malic, tartaric and citric acids and, generally speaking, are fruit acids, 2-hydroxylalkanoic, mandelic and salicylic acids, as well as their alkylated or acylated derivatives such as 5-n-octanoylsalicylic acid, 5-n-dodecanoylsalicylic acid, 5-n-decanoyl-salicylic acid, 5-n-octylsalicylic acid, 5- or 4-n-heptyloxysalicylic acid, 2-hydroxy-3-methylbenzoic acid, or alternatively their alkoxylated derivatives such as 2-hydroxy-3-methoxybenzoic acid.

The retinoids can especially be retinoic acid (all-trans or 13-cis) and its derivatives, retinol (vitamin A) and its esters such as retinol palmitate, retinol acetate and retinol propionate as well as their salts, or alternatively retinal.

By way of example, hydroxy acids, the keto acids and the retinoids can be used in the compositions according to the invention in a quantity representing from 0.1 to 5% by weight of the total weight of the composition and, better, from 0.5 to 3%.

For the purpose of effectively combating photo-ageing, it is additionally possible to add to the composition of the invention one or more hydrophilic or lipophilic complementary solar filters, which are active in the UVA and/or the UVB.

An in vitro test of efficacy of desquamation has been carried out on keratinocytes using 5-n-octanoylsalicylic acid (compound 1), S-carboxymethylcysteine (compound 2), the bis(1-ethoxycarbonylethyl) ester of nonanedioic acid (compound 3), 2-acetoxy-5-octanoylbenzoic acid (compound 4) and 5-oxothiomorpholine-3-carboxylic acid (compound 5).

The principle of the test is based on the fact that desquamation induces the release of corneocytes. The greater the desquamation power of the product tested, the greater the number of corneocytes released.

The protocol of the test was as follows:

keratinocytes were obtained from skin biopsies by separation of the epidermis, dissociated by enzymatic action with trypsin and cultured at a concentration of $2\times10^{-5}$ cells/ml. Growth and differentiation of the keratinocytes were obtained by culture for 10 to 20 days in a specific medium.

Then, after removal of the culture medium, the product to be tested was added and the activity of the product was evaluated. To do this, two samples were taken at $T_0$ and $T_{60}$, that is to say before the addition of the product and 60 minutes after this addition, and the samples thus taken were analysed in a flow cytometer in order to count the population of corneocytes. The corneocyte and keratinocyte populations are differentiated in the flow cytometer by treatment with Acridine Orange which is specific for the DNA of the cells and which binds to the nucleus of the cells and thus exclusively reveals the presence of the keratinocytes.

The cell detachment index is determined by the difference between $T_{60}$ and $T_0$.

The same measurement was carried out for a control not containing product to be tested because the experiment inevitably causes the liberation of corneocytes, even in the absence of active agent. The variation in the control arbitrarily fixed the standard of 100%.

The results are collated in the table below:

| Control | Compound 1 | Compound 2 | Compound 3 | Compound 4 | Compound 5 |
|---|---|---|---|---|---|
| 0% | 106% | 121% | 59% | inactive | inactive |

These results show clearly that S-carboxymethylcysteine, at a concentration equal to that of 5-n-octanoylsalicylic acid which is known as being a powerful desquamating active agent, is much more active than the latter, and that the other compounds have weaker activities than that of S-carboxymethylcysteine.

A further subject of the invention is a non-therapeutic process for treatment of the skin intended for the desquamation of the skin, consisting in applying to the skin a composition containing at least one carboxylic acid carrying a thioether function, a sulphoxide function or a sulphone function and especially an acid corresponding to one of the formulae (I), (II) or (III), in the free state or partially neutralized, in a cosmetically and/or dermatologically acceptable medium.

Another subject of the invention is a process for cosmetic or dermatological treatment of the ageing of the skin, consisting in applying to the skin a composition containing at least one acid such as defined above, in a cosmetically and/or dermatologically acceptable medium.

The composition of the invention contains a cosmetically or dermatologically acceptable medium, that is to say a medium compatible with the skin, the nails, the mucous membranes, the tissues and the hair. The composition containing the acid carrying a thioether function, a sulphoxide function or a sulphone function can be applied topically to the face, the neck, the hair, the mucous membranes and the nails or any other cutaneous region of the body.

The compositions according to the invention can be present in all of the forms appropriate for topical application, especially in the form of aqueous, aqueous/alcoholic or oily solutions, of dispersions of the lotion or serum type, of aqueous, anhydrous or oily gels, of emulsions of liquid or semi-liquid consistency of the milk type, obtained by dispersion of a fatty phase in an aqueous phase (O/W) or conversely (W/O), of suspensions or emulsions of soft, semi-solid or solid consistency of the cream or gel type, of microemulsions or alternatively of microcapsules, of microparticles or of vesicular dispersions of ionic and/or non-Ionic type. These compositions are prepared according to the usual methods.

They can likewise be used for the hair in the form of aqueous, alcoholic or aqueous/alcoholic solutions, or in the form of creams, of gels, of emulsions, of foams or alternatively in the form of aerosol compositions likewise containing a propellant under pressure.

The quantities of the different constituents of the compositions according to the invention are those conventionally used in the fields under consideration.

These compositions especially form protection, treatment or care creams for the face, for the hands or for the body, protection or care body milks, lotions, gels or foams for the care of the skin and mucous membranes or for cleansing the skin.

The compositions can likewise consist of solid preparations forming soaps or cleansing bars.

When the composition of the invention is an emulsion, the proportion of the fatty phase can range from 5% to 80% by weight, and preferably from 5% to 50% by weight with respect to the total weight of the composition. The oils, the emulsifiers and the co-emulsifiers used in the composition in emulsion form are chosen from those conventionally used in the cosmetic or dermatological field. The emulsifier and the co-emulsifier are present, in the composition, in a proportion ranging from 0.3% to 30% by weight and preferably from 0.5 to 20% by weight with respect to the total weight of the composition. The emulsion can, in addition, contain lipid vesicles.

When the composition is an oily solution or an oily gel, the quantity of oil can range up to more than 90% by weight of the total weight of the composition.

In a known manner, the composition of the invention can likewise contain adjuvants customary in the cosmetic and dermatological fields, such as hydrophilic or lipophilic gelling agents, hydrophilic or lipophilic active agents, preservatives, antioxidants, solvents, perfumes, sequestering agents, fillers and colouring materials. The quantities of these different adjuvants are those conventionally used in the fields under consideration, for example from 0.01% to 20% of the total weight of the composition. These adjuvants, according to their nature, can be introduced into the fatty phase, into the aqueous phase and/or into lipid spherules.

As oils which can be used in the invention, mention may be made of mineral oils (liquid petrolatum), vegetable oils (karite oil, sweet almond oil), animal oils, synthetic oils, silicone oils (cyclomethicone) and fluorinated oils (perfluoropolyethers). It is also possible to use, as fatty materials, fatty alcohols, fatty acids (stearic acid), or waxes (paraffin, carnauba, beeswax).

As emulsifiers which can be used in the invention, mention may be made of Polysorbate 60 and sorbitan stearate sold respectively under the trade names Tween 60 and Span 60 by the company ICI. It is also possible to use PEG 20 stearate, marketed by the company ICI under the brand MYRJ.

As solvents which can be used in the invention, mention may be made of lower alcohols, especially ethanol and isopropanol, and propylene glycol.

As hydrophilic gelling agents, mention may be made of carboxyvinyl polymers (carbomer), acrylic copolymers such as acrylate/alkylacrylate copolymers, polyacrylamides, polysaccharides such as hydroxypropylcellulose, natural gums (xanthan) and clays, and, as lipophilic gelling agents, mention may be made of modified clays, such as bentones, metallic salts of fatty acids such as aluminium stearates, hydrophobic silica, polyethylenes and ethylcellulose.

As hydrophilic active agents, proteins or protein hydrolysates, amino acids, polyols, urea, allantoin, sugars and sugar derivatives, water-soluble vitamins, starch, bacterial or vegetable extracts, especially of Aloe Vera, or antiseptics.

As lipophilic active agents, it is possible to use tocopherol (vitamin E) and its derivatives, essential fatty acids, ceramides or essential oils.

It is possible, inter alia, to combine the acids with active agents intended especially for the prevention and/or for the treatment of cutaneous ailments. Among these active agents, it is possible to mention by way of example:

- agents modulating cutaneous differentiation and/or proliferation and/or pigmentation, such as vitamin D and its derivatives, oestrogens such as oestradiol, kojic acid, or hydroquinone;
- anti-free radical agents, such as α-tocopherol or its esters, superoxide dismutases, certain metal chelating agents or ascorbic acid and its esters.

It is possible, in addition, to combine with the acids of the invention antagonists of substance P and/or of CGRP (Calcitonin Gene-Related Peptide or peptide linked to the calcitonin gene) such as Iris Pallida and strontium salts, especially the chlorides and the nitrates of strontium, or of antagonists of substance P and/or of CGRP such as those described in the French Patent Applications filed in the name of the Applicant under the numbers 9405537 and 9500900. Such a combination allows a perfect tolerance of these compositions to be guaranteed, even by very sensitive skins.

The cosmetic or dermatological treatment process of the invention can be carried out, especially, by applying the hygienic, cosmetic or dermatological compositions such as those defined above according to the technique of use customary for these compositions. For example: application of creams, of gels, of serums, of ointments, of lotions or of milks to the skin, the scalp, the nails and/or the mucuous membranes.

The following examples illustrate the invention. In these examples, the proportions indicated are percentages by weight.

EXAMPLE 1

Stabilizing Lotion

| | |
|---|---|
| S-carboxymethylcysteine | 2% |
| Bactericide | 0.1% |
| Triethanolamine | 1.7% |
| Sequestering agent | 0.1% |
| Transcutol (Gattefosse) | 5% |
| Ethanol | 10.6% |
| Water | 80.5% |

A lotion is obtained which, applied daily to the skin of the face, allows an improvement in the suppleness and in the elasticity of the treated skin to be observed.

EXAMPLE 2

Colourless Cleansing Cream

| | |
|---|---|
| Allantoin | 0.1% |
| S-carboxymethylcysteine | 1% |
| Glycerol stearate | 1.2% |
| Oils | 12% |
| Wax | 2% |
| Preservative | 0.3% |
| Antiseptic | 0.2% |
| Perfume | 0.4% |
| Triethanolamine | 0.8% |
| Water | qsp 100 |
| PEG 20 stearate | 6.6% |
| Ethanol | 4.2% |

A cream is obtained which, on regular application, allows skin spots to be reduced by desquamation.

EXAMPLE 3

Astringent Lotion

| | |
|---|---|
| S-carboxymethylcysteine | 2% |
| Colourant | 0.00008% |
| Perfume | 0.08% |
| Ethyl alcohol | 16.60% |
| Preservative | 0.20% |
| Triethanolamine | 1.5% |
| Sequestering agent | 0.1% |
| Extra-light precipitated magnesium carbonate | 0.08% |
| Water | qsp 100 |
| Ethanol | 16.6% |

Application of this solution under dermatological control allows a deep desquamation of the horny layer to be obtained and, thus, the bringing into play of an epidermal repair process, having as its final therapeutic effect an erasure of spots and dyschromias, a reduction in wrinkles and lines and an improvement in the clinical state of the skin, which takes on the appearance of a younger skin.

This application is made at a rate of one to three weekly sessions for 4 to 6 weeks.

EXAMPLE 4

Astringent Lotion

This example differs from Example 3 by the addition of 0.25% of strontium nitrate. This formula is particularly suitable for the treatment of sensitive skins.

What is claimed is:

1. A method of desquamating skin and/or promoting epidermal renewal in skin, comprising applying to the skin an effective amount of at least one carboxylic acid and/or a salt thereof represented by formula (I) (II) or (III):

(I)

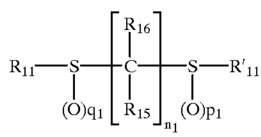

(II)

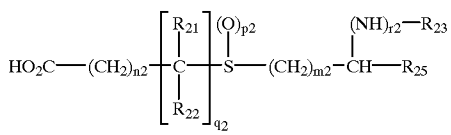

(III)

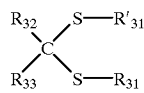

wherein n is an integer of a value ranging from 1 to 10, $p_1$ and $q_1$, which are identical or different, are 0, 1 or 2, $n_2$ is an integer of a value ranging from 0 to 5, $p_2$ is 0, 1 or 2, $q_2$ is 0, 1 or 2, $q_2$ is 0, 1, 2 or 3, $m_2$ is an integer of a value ranging from 0 to 10, $r_2$ is 0 or 1, $q_2$ and $n_2$ never both being zero simultaneously, $R_{11}$ and $R'_{11}$, which are identical or different, are a radical selected from the group consisting of a)

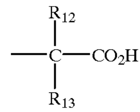

b)

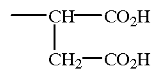

c)

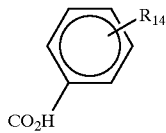

wherein $R_{12}$ and $R_{13}$, which are identical or different, are selected from the group consisting of a hydrogen atom and $C_1$–$C_8$ linear or branched alkyl or alkenyl radicals;

$R_{14}$ is selected from the group consisting of a hydrogen atom, linear or branched $C_1$–$C_8$ alkyl radicals, linear or branched $C_1$–$C_8$ alkenyl radicals and linear and branched $C_1$–$C_8$ alkoxy radicals;

$R_{15}$ and $R_{16}$ are selected from the group consisting of a hydrogen atom and linear or branched $C_1$–$C_8$ alkoxy radicals;

$R_{21}$ and $R_{22}$ are selected from the group consisting of a hydrogen atom and linear or branched $C_1$–$C_6$ alkoxy and alkenyl radicals, phenyl, $C_1$–$C_6$ alkylcarboxylic and $C_1$–$C_6$ alkenylcarboxylic acid radicals;

$R_{23}$ is a $C_1$–$C_{17}$ linear or branched alkyl or alkenyl radical or an acyl radical —CO—$R_{24}$, where $R_{24}$ is a $C_1$–$C_{17}$ linear or branched alkyl or alkenyl radical;

$R_{25}$ is selected from the group consisting of a hydrogen atom, a $C_1$–$C_6$ linear or branched alkyl and alkenyl radical, a $C_1$–$C_5$ alkyl-carboxylic acid radical, $C_1$–$C_5$ alkenylcarboxylic acid radical and the function —COOH;

$R_{31}$ and $R'_{31}$ are selected from the group consisting of

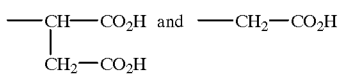

$R_{32}$ is a radical selected from the group consisting of i) —$CH_3$ ii) —$CO_2H$ iii)

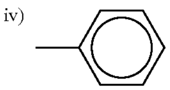

iv)

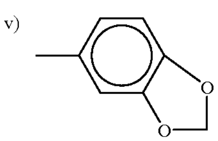

v)

vi)

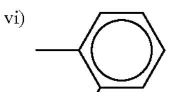

vii)

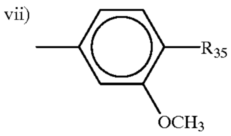

wherein $R_{34}$ is a radical selected from the group consisting of —$CH_2$—$CO_2H$ and —CO—$CH_3$, and $R_{35}$ is a radical selected from the group consisting of OH, $OCH_3$, $OC(CH_3)_3$, and $OCH_2CO_2H$, $R_{33}$ is a radical selected from the group consisting of a hydrogen atom, a $C_1$–$C_6$ linear or branched alkyl or alkenyl radical, or $R_{32}$ and $R_{33}$ together form an alkane diyl radical —$(CH_2)_{m_3}$— wherein $m_3$ represents an integer of a value ranging from 3 to 5, or $R_{32}$ and $R_{33}$ together form an aralkanediyl radical represented by the formula

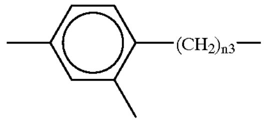

wherein $n_3$ is 3 or 4.

2. The method of claim 1, which is desquamating skin.

3. The method of claim 1, which is promoting epidermal renewal in skin.

4. The method of claim 1, wherein at least a portion of the carboxylic acid is in the form of a salt.

5. The method of claim 1, wherein the acids are selected from the group consisting of (a) compounds corresponding to formula (I) in which $R_{15}=R_{16}=H$, $p_1=q_1$ and $R_{11}=R'_{11}$, (b) compounds corresponding to formula (II) in which $r_2=1$, $R_{23}=H$, $R_{25}$=—COOH and m=1 (cysteine derivatives) or m=2, and (c) compounds corresponding to formula (III) in which $R_{32}$ is an aromatic radical, $R_{33}=H$ and $R_{31}=R'_{31}$.

6. The method of claim 1, wherein the acid is selected from the group consisting of 2,2'-dithiomethylenedibenzoic acid,
2,2'-dithioethylenedibenzoic acid,
2,2'-disulphinylethylenedibenzoic acid,
2,2'-(dithiopropane-1,3-diyl)dibenzoic acid,
2,2'-(dithiobutane-1,4-diyl)dibenzoic acid,
2,2'-(dithiopentane-1,5-diyl)dibenzoic acid,
2,2'-(dithiohexane-1,6-diyl)dibenzoic acid,
2,2'-(disulphinylhexane-1,6-diyl)dibenzoic acid,
α,α'-(dithiohexane-1,6-diyl)disuccinic acid,
2,2'-(dithiooctane-1,8-diyl)dibenzoic acid,
2,2'-(dithiodecane- 1,10-diyl)dibenzoic acid,
α,α'-(dithiodecane- 1,10-diyl )disuccinic acid,
α,α'-dithiomethylenediacetic acid,
α,α'-dithioethylenediacetic acid,
α,α'-disulphinylethylenediacetic acid,
α,α'-disulphonylethylenediacetic acid,
α,α'-(dithiohexane-1,6-diyl)diacetic acid,
α,α'-(disulphinylhexane-1,6-diyl)diacetic acid,
α,α'-(disulphonylhexane-1,6-diyl)diacetic acid,
α,α'-(dithiodecane-1,10-diyl)diacetic acid,
α,a'-(disulphinyldecane-1,10-diyl)diacetic acid,
α,α'-(disulphonyldecane-1,10-diyl)diacetic acid,
S-(carboxymethyl)cysteine,
S-(carboxyethyl)cysteine,
S-(4-carboxybutyl)cysteine,
S-(carboxymethyl)sulphinylcysteine,
S-(carboxymethyl)sulphonylcysteine,
S-(1-carboxy-1-ethyl)cysteine,
S-(2-carboxy-2-propyl)cysteine,
α,α'-(p-methoxybenzylidenedithio)disuccinic acid,
α,α'-(benzylidenedithio)disuccinic acid,
α,α'-(piperonylidenedithio)disuccinic acid,
α,α'-(vanillylidenedithio)disuccinic acid,
α,α'-(veratrylidenedithio)disuccinic acid,
α,α'-(4-butoxy-3-methoxybenzylidenedithio)disuccinic acid,
α,α'-(4-carboxymethyloxy-3-methoxybenzylidenedithio) disuccinic acid,
α,α'-(p-methoxybenzylidenedithio)diacetic acid,
α,α'-(benzylidenedithio)diacetic acid,
α,α'-(piperonylidenedithio)diacetic acid,
α,α'-(vanillylidenedithio)diacetic acid, and
α,α'-(veratrylidenedithio)diacetic acid,
or a salt thereof.

7. The method of claim 1, wherein the acid is S-carboxymethylcysteine or an of inorganic or organic base mono- or disalt thereof.

8. The method of claim 1, wherein the acid is applied to the skin as a topically acceptable composition, wherein the composition comprises from 0.2 to 20% by weight of the acid, based on the total weight of the composition.

9. The method of claim 8, wherein the composition comprises from 0.5 to 5% by weight of the acid, based on the total weight of the composition.

10. The method of claim 8, wherein the composition further comprises at least one active agent selected from the group consisting of α- or β-hydroxy acids, α- or β-keto acids, and retinoids.

11. The method of claim 8, wherein the composition further comprises at least one active agent selected from the group consisting of the glycolic, lactic, malic, tartaric, citric, 2-hydroxyalkanoic, mandelic or salicylic acids, and 5-n-octanoylsalicylic acid.

12. The method of claim 10, wherein the composition comprises from 0.1 to 5% by weight of the active agent, based on the total weight of the composition.

13. The method of claim 11, wherein the composition comprises from 0.1 to 5% by weight of the active agent, based on the total weight of the composition.

14. The method of claim 8, wherein the composition further comprises at least one adjuvant selected from the group consisting of proteins or protein hydrolysates, amino acids, polyols, urea, sugars and sugar derivatives, vitamins, starch, vegetable extracts, essential fatty acids, ceramides, and essential oils.

15. The method of claim 8, wherein the composition is an aqueous, oily or aqueous/alcoholic solution, a water-in-oil or oil-in-water emulsion, a microemulsion, an aqueous or anhydrous gel, a serum or dispersion of vesicles, of micro-capsules or of microparticles.

16. The method of claim 8, wherein the composition further comprises at least one antagonist of substance P and/or of CGRP.

17. The method of claim 16, wherein the antagonist is a strontium salt.

18. The method of claim 1, wherein the carboxylic acid, or the salt thereof, has a thioether function.

19. The method of claim 1, wherein the carboxylic acid, or the salt thereof, has a sulphoxide function.

20. The method of claim 1, wherein the carboxylic acid, or the salt thereof, has a sulphone function.

21. A method of treating cutaneous aging in skin comprising applying to the skin an effective amount of at least one carboxylic acid and/or a salt thereof represented by formula (I) (II) or (III):

(I)

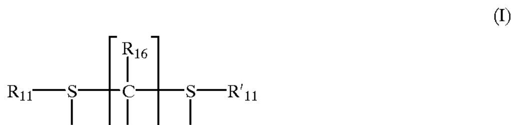

(II)

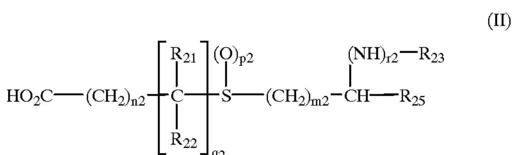

-continued (III)

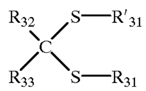

wherein n is an integer of a value ranging from 1 to 10, $p_1$ and $q_1$, which are identical or different, are 0, 1 or 2, $n_2$ is an integer of a value ranging from 0 to 5, $p_2$ is 0, 1 or 2, $q_2$ is 0, 1 or 2, $q_2$ is 0, 1, 2 or 3, $m_2$ is an integer of a value ranging from 0 to 10, $r_2$ is 1, $q_2$ and $n_2$ never both being zero simultaneously, $R_{11}$ and $R'_{11}$, which are identical or different, are a radical selected from the group consisting of a)

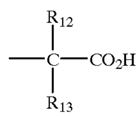

b)

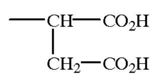

c)

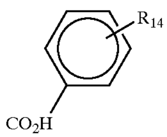

wherein $R_{12}$ and $R_{13}$, which are identical or different, are selected from the group consisting of a hydrogen atom and $C_1$–$C_8$ linear or branched alkyl or alkenyl radicals;

$R_{14}$ is selected from the group consisting of a hydrogen atom, linear or branched $C_1$–$C_8$ alkyl radicals, linear or branched $C_1$–$C_8$ alkenyl radicals and linear and branched $C_1$–$C_8$ alkoxy radicals;

$R_{15}$ and $R_{16}$ are selected from the group consisting of a hydrogen atom and linear or branched $C_1$–$C_8$ alkoxy radicals;

$R_{21}$ and $R_{22}$ are selected from the group consisting of a hydrogen atom and linear or branched $C_1$–$C_6$ alkoxy and alkenyl radicals, phenyl, $C_1$–$C_6$ alkylcarboxylic and $C_1$–$C_6$ alkenylcarboxylic acid radicals;

$R_{23}$ is a $C_1$–$C_{17}$ linear or branched alkyl or alkenyl radical or an acyl radical —CO—$R_{24}$, where $R_{24}$ is a $C_1$–$C_{17}$ linear or branched alkyl or alkenyl radical;

$R_{25}$ is selected from the group consisting of a hydrogen atom, a $C_1$–$C_6$ linear or branched alkyl and alkenyl radical, a $C_1$–$C_5$ alkyl-carboxylic acid radical, $C_1$–$C_5$ alkenylcarboxylic acid radical and the function —COOH;

$R_{31}$ and $R'_{31}$ are selected from the group consisting of

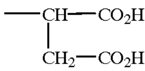

and

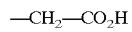

$R_{32}$ is a radical selected from the group consisting of i) $—CH_3$ ii) $—CO_2H$ iii)

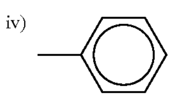

iv)

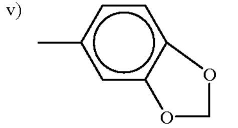

v)

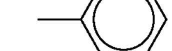

vi)

vii)

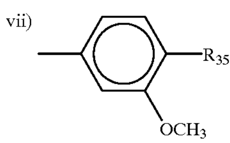

wherein $R_{34}$ is a radical selected from the group consisting of $—CH_2—CO_2H$ and $—CO—CH_3$, and $R_{35}$ is a radical selected from the group consisting of OH, $OCH_3$, $OC(CH_3)_3$, and $OCH_2CO_2H$, $R_{33}$ is a radical selected from the group consisting of a hydrogen atom, a $C_1$–$C_6$ linear or branched alkyl or alkenyl radical, or $R_{32}$ and $R_{33}$ together form an alkane diyl radical $—(CH_2)m_3—$ wherein $m_3$ represents an integer of a value ranging from 3 to 5, or $R_{32}$ and $R_{33}$ together form an aralkanediyl radical represented by the formula

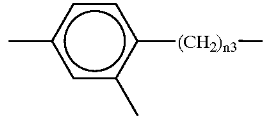

wherein $n_3$ is 3 or 4.

22. The method of claim 21, wherein the acids are selected from the group consisting of (a) compounds corresponding to formula (1) in which $R_{15}=R_{16}=H$, $p_1=q_1$ and $R_{11}=R'_{11}$, (b) compounds corresponding to formula (II) in which $r_2=1$, $R_{23}=H$, $R_{25}=—COOH$ and m=1 (cysteine derivatives) or m=2, and (c) compounds corresponding to formula (III) in which $R_{32}$ is an aromatic radical, $R_{33}=H$ and $R_{31}=R'_{31}$.

23. The method of claim 21, wherein the acid is selected from the group consisting of 2,2'-dithiomethylenedibenzoic acid,
2,2'-dithioethylenedibenzoic acid,
2,2'-disulphinylethylenedibenzoic acid,
2,2'-(dithiopropane-1,3-diyl)dibenzoic acid,
2,2'-(dithiobutane-1,4-diyl)dibenzoic acid,
2,2'-(dithiopentane-1,5-diyl)dibenzoic acid,
2,2'-(dithiohexane-1,6-diyl)dibenzoic acid,
2,2'-(disulphinylhexane-1,6-diyl)dibenzoic acid,
α,α'-(dithiohexane-1,6-diyl)disuccinic acid,
2,2'-(dithiooctane-1,8-diyl)dibenzoic acid,
2,2'-(dithiodecane-1,10-diyl)dibenzoic acid,
α,α'-(dithiodecane-1,10-diyl)disuccinic acid,
α,α'-dithiomethylenediacetic acid,
α,α'-dithioethylenediacetic acid,
α,α'-disulphinylethylenediacetic acid,
α,α'-disulphonylethylenediacetic acid,
α,α'-(dithiohexane-1,6-diyl)diacetic acid,
α,α'-(disulphinylhexane-1,6-diyl)diacetic acid,
α,α'-(disulphonylhexane-1,6-diyl)diacetic acid,
α,α'-(dithiodecane- 1,10-diyl)diacetic acid,
α,α'-(disulphinyldecane- 1,10-diyl)diacetic acid,
α,α'-(disulphonyldecane- 1,10-diyl)diacetic acid,
S-(carboxymethyl)cysteine,
S-(carboxyethyl)cysteine,
S-(4-carboxybutyl)cysteine,
S-(carboxymethyl)sulphinylcysteine,
S-(carboxymethyl)sulphonylcysteine,
S-(1-carboxy-1-ethyl)cysteine,
S-(2-carboxy-2-propyl)cysteine,
α,α'-(p-methoxybenzylidenedithio)disuccinic acid,
α,α'-(benzylidenedithio)disuccinic acid,
α,α'-(piperonylidenedithio)disuccinic acid,
α,α'-(vanillylidenedithio)disuccinic acid,
α,α'-(veratrylidenedithio)disuccinic acid,
α,α'-(4-butoxy-3-methoxybenzylidenedithio)disuccinic acid,
α,α'-(4-carboxymethyloxy-3-methoxybenzylidenedithio) disuccinic acid,
α,α'-(p-methoxybenzylidenedithio)diacetic acid,
α,α'-(benzylidenedithio)diacetic acid,
α,α'-(piperonylidenedithio)diacetic acid,
α,α'-(vanillylidenedithio)diacetic acid, and
α,α'-(veratrylidenedithio)diacetic acid,
or a salt thereof.

24. The method of claim 21, wherein the acid is S-carboxymethylcysteine or an inorganic or organic base mono- or disalt thereof.

25. The method of claim 21, wherein the acid is applied to the skin as a topically acceptable composition, wherein the composition comprises from 0.2 to 20% by weight of the acid, based on the total weight of the composition.

26. The method of claim 25, wherein the composition comprises from 0.5 to 5% by weight of the acid, based on the total weight of the composition.

27. The method of claim 25, wherein the composition further comprises at least one active agent selected from the group consisting of α- or β-hydroxy acids, α- or β-keto acids, and retinoids.

28. The method of claim 25, wherein the composition further comprises at least one active agent selected from the group consisting of the glycolic, lactic, malic, tartaric, citric, 2-hydroxyalkanoic, mandelic and salicylic acids, and 5-n-octanoylsalicylic acid.

29. The method of claim 27, wherein the composition comprises 0.1 to 5% by weight of the active agent, based on the total weight of the composition.

30. The method of claim 28, wherein the composition comprises from 0.1 to 5% by weight of the active agent, based on the total weight of the composition.

31. The method of claim 25, wherein the composition further comprises at least one adjuvant selected from the group consisting of proteins and protein hydrolysates, amino acids, polyols, urea, sugars and sugar derivatives, vitamins, starch, vegetable extracts, essential fatty acids, ceramides, and essential oils.

32. The method of claim 25, wherein the composition is an aqueous, oily or aqueous/alcoholic solution, a water-in-oil or oil-in-water emulsion, a microemulsion, an aqueous or anhydrous gel, a serum or dispersion of vesicles, of microcapsules or of microparticles.

33. The method of claim 25, wherein the composition further comprises at least one antagonist of substance P and/or of CGRP.

34. The method of claim 33, wherein the antagonist is a strontium salt.

35. The method of claim 21, wherein the carboxylic acid, or salt thereof, has a thioether function.

36. The method of claim 21, wherein the carboxylic acid, or the salt thereof, has a sulphoxide function.

37. The method of claim 21, wherein the carboxylic acid, or the salt thereof, has a sulphone function.

* * * * *